(12) United States Patent
Robertson et al.

(10) Patent No.: US 7,872,749 B2
(45) Date of Patent: Jan. 18, 2011

(54) INSTRUMENT FOR MAKING OPTICAL MEASUREMENTS ON MULTIPLE SAMPLES RETAINED BY SURFACE TENSION

(75) Inventors: Charles William Robertson, Rockland, DE (US); Thomas A. Tokash, Chesapeake City, MD (US); Paul S. Zdinak, Kennett Square, PA (US)

(73) Assignee: Nanodrop Technologies LLC, Wilmington, DE (US)

(*) Notice: Subject to any disclaimer, the term of this patent is extended or adjusted under 35 U.S.C. 154(b) by 261 days.

(21) Appl. No.: 12/293,539

(22) PCT Filed: Mar. 15, 2007

(86) PCT No.: PCT/US2007/006457

§ 371 (c)(1),
(2), (4) Date: Sep. 18, 2008

(87) PCT Pub. No.: WO2007/111838

PCT Pub. Date: Oct. 4, 2007

(65) Prior Publication Data

US 2009/0059225 A1    Mar. 5, 2009

Related U.S. Application Data

(60) Provisional application No. 60/785,208, filed on Mar. 23, 2006.

(51) Int. Cl.
*G01J 3/28* (2006.01)
(52) U.S. Cl. ...................................... 356/326
(58) Field of Classification Search ......... 356/317–318, 356/326, 417
See application file for complete search history.

(56) References Cited

U.S. PATENT DOCUMENTS

| | | | |
|---|---|---|---|
| 4,643,580 A * | 2/1987 | Gross et al. | 356/440 |
| 5,210,590 A * | 5/1993 | Landa et al. | 356/328 |
| 6,809,826 B2 | 10/2004 | Robertson | |
| 7,375,815 B2 * | 5/2008 | Kralik | 356/440 |
| 2008/0002181 A1 * | 1/2008 | Robertson et al. | 356/317 |

FOREIGN PATENT DOCUMENTS

| | | |
|---|---|---|
| CN | 1421718 | 6/2003 |
| CN | 1494655 | 5/2004 |
| EP | 0 574 686 A2 | 12/1993 |

* cited by examiner

*Primary Examiner*—Kara E Geisel
(74) *Attorney, Agent, or Firm*—Charles B. Katz; Michael C. Staggs

(57) ABSTRACT

The invention is an installment for making multi-channel spectroscopic measurements on a plurality of nanodrop samples held by surface tension between opposing optical fibers wherein a single fiber is scanned across a linear spaced array of receiving, detecting fibers.

14 Claims, 5 Drawing Sheets

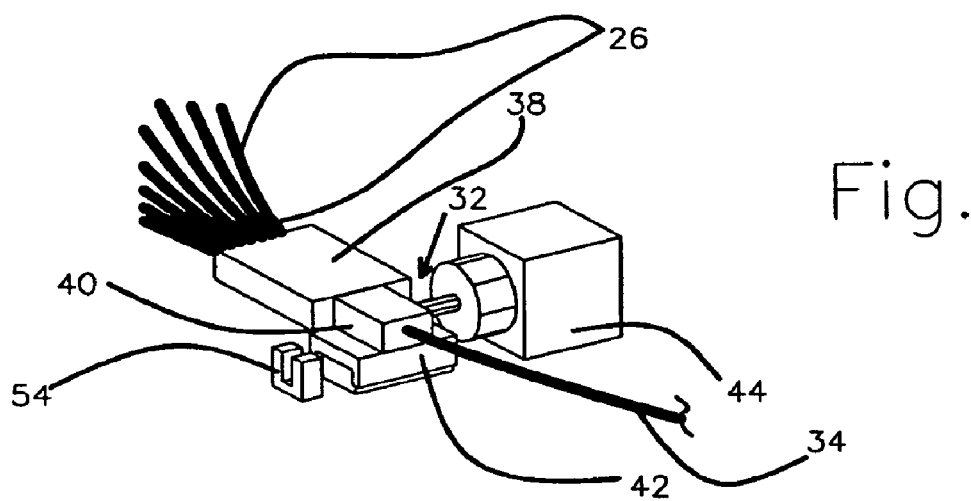
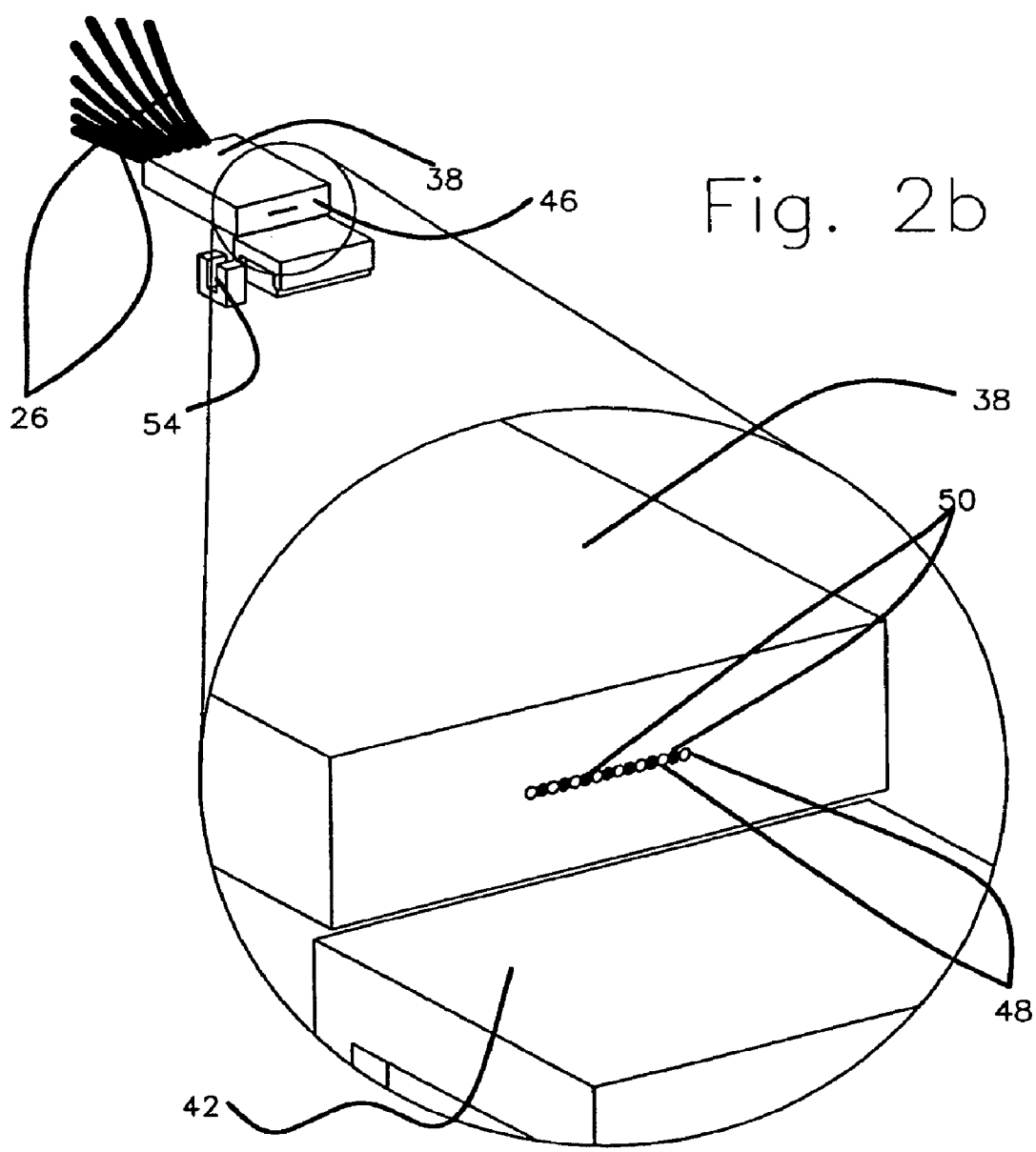

INSTRUMENT FOR MAKING OPTICAL MEASUREMENTS ON MULTIPLE SAMPLES RETAINED BY SURFACE TENSION

CROSS-REFERENCE TO RELATED APPLICATIONS

This application is a National Stage application under 35 U.S.C. §371 of PCT Application No. PCT/US2007/006457, filed Mar. 15, 2007, entitled "Instrument For Making Optical Measurements On Multiple Samples Retained By Surface Tension", which claims the priority benefit of U.S. Provisional Application No. 60/785,208, filed Mar. 23, 2006, entitled "Eight-Channel Instrument", which applications are incorporated herein by reference in their entireties.

FIELD OF THE INVENTION

This invention relates to the field of optical measurements and particularly to spectrophotometry and more particularly to such measurements made upon liquid drops on the order of 2 microliters or less.

BACKGROUND OF THE INVENTION

Robertson, in U.S. Pat. Nos. 6,628,382 and 6,809,826, teaches containment of small droplets by surface tension. These patents are incorporated in their entirety by reference. In addition the method and apparatus disclosed may be applied to fluorometry with apparatus and method as taught in Robertson et al.'s application PCT/US 2006/04406 with inclusion of the special optical requirements in fluorometry to keep the signal from being overwhelmed by incident light. The disclosure of that application is incorporated herein in its entirety by reference.

In making these measurements, the need for high productivity in the work of the laboratory involved is plain. Instrumentation and method that permit simultaneous, or near simultaneous, operation on multiple samples is most desirable. It is to this end that this invention is directed.

SUMMARY OF THE INVENTION

In brief, the invention is directed to processing in an optical measuring device a plurality of small droplets of liquid ("nanodrops" of micro-liter volume) simultaneously or nearly so. The preferred embodiment of the invention has eight fibers, which preferably are 100 micron, individually picking up light from a flash lamp and feeding the upper fiber bushings of an array of eight paired measurement fiber optic (FO) bushings. Light from the eight receiving fibers, which preferably are 400 micron, is fed to a fiber optic switch or multiplexer where a precision linear actuator scans a single 400-micron fiber across the spaced ends of the eight sample-signal-receiving fibers. The fibers are spaced in the multiplexer by interleaving dead fibers (in the expanded view seen in FIG. 2b these dead fibers are shown as black circles which is a long used industry practice) or can be spaced with the use of a micro machined V-groove block or by packing custom coated fibers into a cavity machined to be an exact fit.

Unlike the prior art apparatus disclosed in U.S. Pat. Nos. 6,628,382 and 6,809,826, the upper arm is moved by a stepper motor or servo motor linear actuator to accommodate the weight of the arm. Like the prior art apparatus, the moveable, upper arm after sample loading is moved to a substantially closed position to spread the samples and wet the opposing anvil surfaces and then to a selected more open position to pull the samples into columns to establish optical paths for optical measurements.

BRIEF DESCRIPTION OF THE DRAWINGS

FIG. 2a is a somewhat schematic partial view in perspective of the scanning apparatus enlarged from FIGS. 1a and b.

FIG. 2b is a somewhat schematic view in perspective of the fiber array with the scanning means removed and shows a further enlargement to show the spacing of the fibers.

DETAILED DESCRIPTION OF THE INVENTION

Figure 1A:
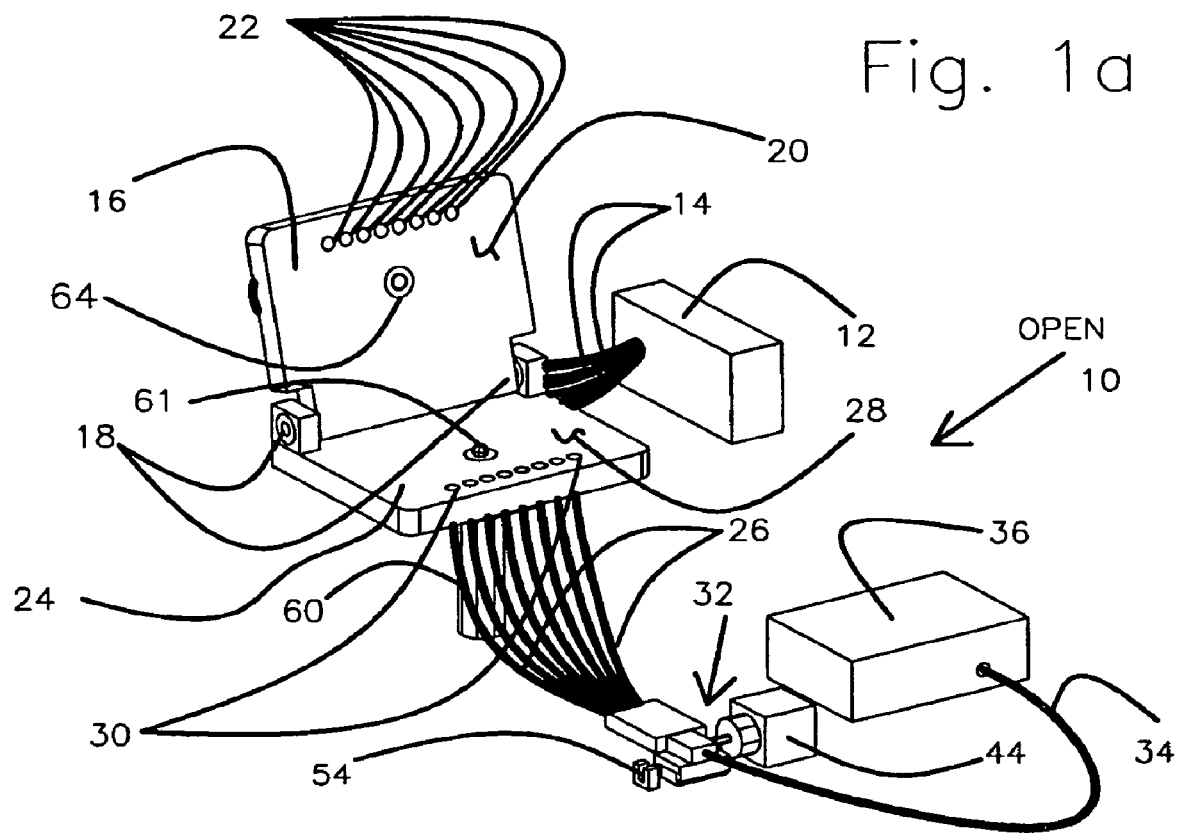
FIG. 1a is a view in perspective of the apparatus in the open position.
Figure 1B:
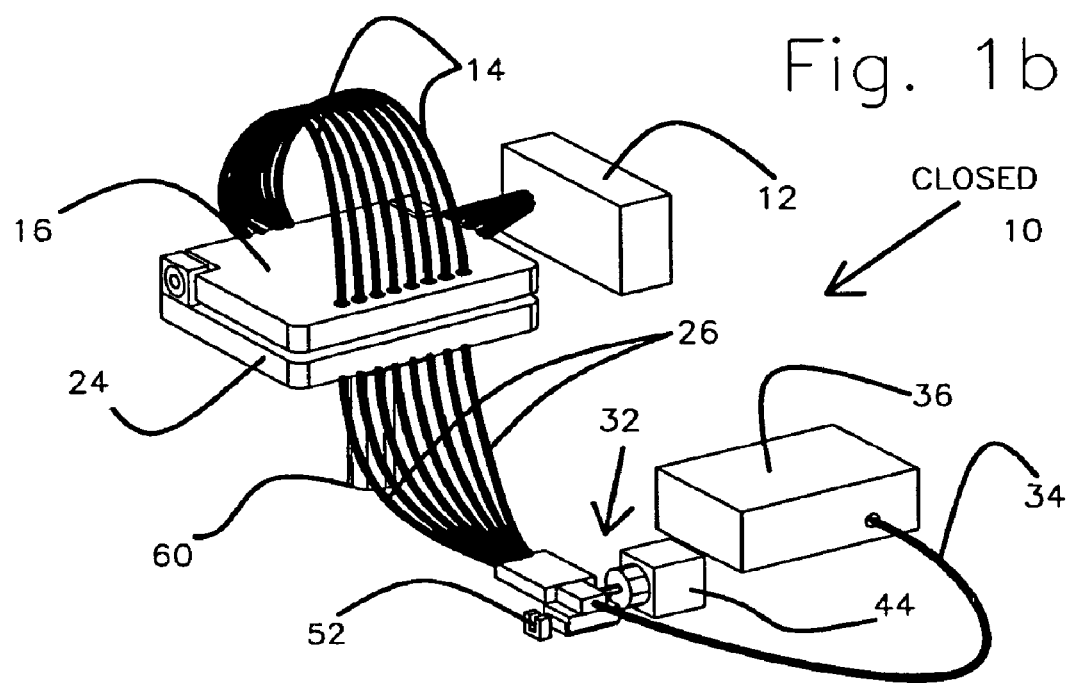
FIG. 1b is a view in perspective of the apparatus in a closed position.

Consider FIG. 1a showing the apparatus of the invention 10 in the open position which is used for loading and FIG. 1b showing it closed either in the first instance where the surfaces are proximate to spread the samples and wet the surfaces or in the measuring position where the surfaces are moved sufficiently apart to pull the samples into liquid columns for measuring. Light is generated in flash-lamp 12. We use a lamp from Hamamatsu of Hamamatsu City, Japan. The light is carried by eight supply fibers 14, preferably 100 micron, to upper arm 16 of the 8-channel measuring instrument 10. The fibers pass through upper arm 16 and are finished proud of the surface 20 of upper arm 16. These form the eight upper anvils 22 of the apparatus. Upper arm 16 is pivotally mounted at 18 to fixed arm 24 which serves as a base for the instrument or can be mounted to a base. Eight receiving/detection fibers 26 pass through fixed arm 24 and are finished so as to stand slightly proud of the surface 28 thereof to form eight lower anvils 30. Preferably the receiving/detecting fibers are 400 micron. These lead to optical switch 32 in which a single fiber 34 is scanned across the eight fibers 26 with apparatus which will be described in detail below—The single scanning fiber 34 leads the signals in turn to measuring means 36, preferably a spectrometer or fluorometer (see FIG. 3).

Consider FIGS. 2a and 2b. Here the scanning mechanism of optical switch 32 is shown in greater detail. In FIG. 2a it is seen that optical switch 32 comprises feed block 38, scanning block 40, base/guide slide assembly 42, and linear actuating mechanism 44.

Feed block 38 holds the ends of fibers 26 in spaced linear array. The fiber ends 48 are finished flush with face 46 of feed block 38. This is seen in more detail in FIG. 2b with both a view in the same scale as FIG. 2a where scanning block 40 is removed and, in greater detail, in the enlarged view. Spacing is provided by inter-leaving active fiber ends 48 with dead fiber ends 50 as seen in the enlargement. "Dead fibers" are simply suitable lengths of fiber not connected to a source. Spacing is important in limiting any cross-talk in reading the signals output by the individual fibers 26. For convenience, the known convention is used showing the ends of the dead fibers as black circles. Feed block 38 in the physical embodiment is an assembly custom made by Romack of Williamsburg, Va.

Scanning block 40 mounted on base/guide slide assembly 42, is constrained by means not shown in detail in base/guide slide assembly 42 to move linearly along the face of feed block 38 so that one end of fiber 34 moves across the eight ends 48 of spaced fibers 26. It is moved by linear actuating mechanism 44. In the physical embodiment of the invention, single opposing fiber 34 is a custom SMA terminated fiber optic patch cord also from Romack.

Figure 5A:
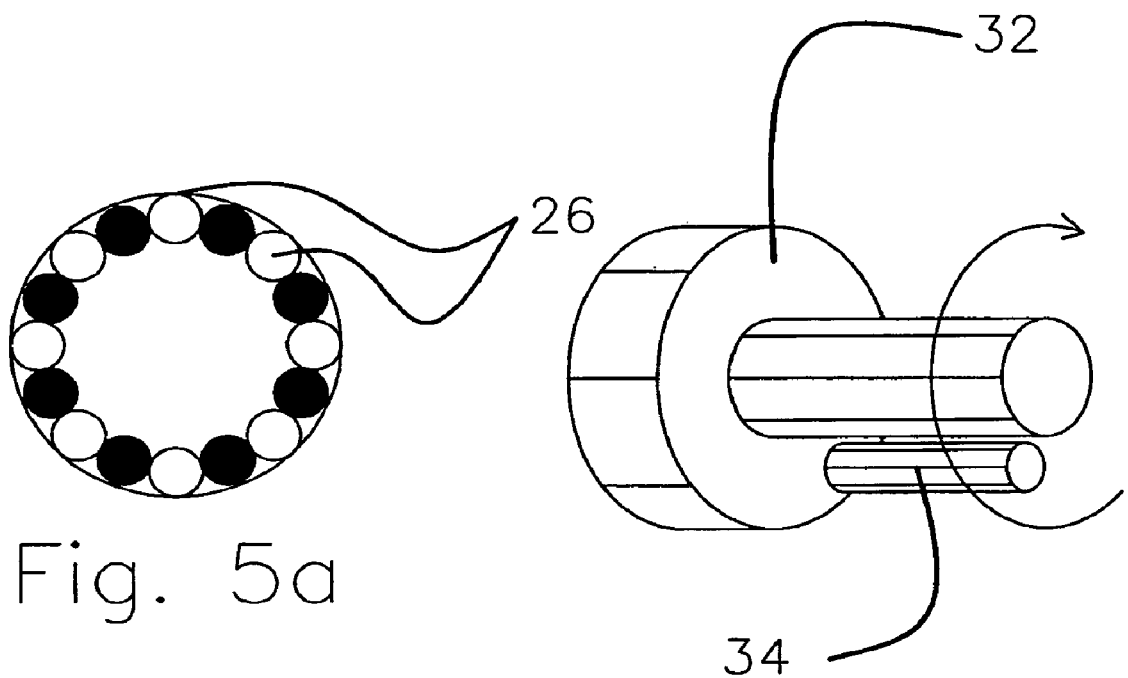
FIGS. 5 a, b, and c show alternate fiber spacing arrangements with 5a also schematically indicating rotary scanning means.
Figure 5B:
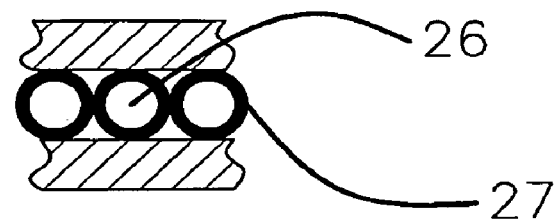
Figure 5C:
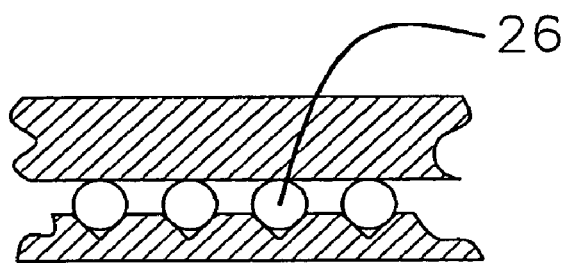

Base guide slide assembly 42 functions to linearly guide scanning block 40 in orthogonal relationship with fiber ends 48. In the physical embodiment it is a ball bearing slide from Deltron of Bethel, Conn. p/n E-1. An end stop detector 54 is provided to establish a reference point for the motion of the scanning block. Linear actuating mechanism 44 is a stepper motor linear actuator. We use one fabricated by Haydon Switch of Waterbury Conn. p/n 28H43-05-036. It is plain to one skilled in the art that the linear array of the embodiment and the linear scanning means 32 described and shown, for example, in FIG. 2b could be replaced by a toroidal array scanned by rotary means 32 carrying scanning fiber 34 as schematically indicated in FIG. 5a. Alternatively the fibers can be spaced by location in V-shaped grooves in the assembly (see FIG. 5c). Still another embodiment would be to use fibers custom coated to yield suitable spacing in a suitable cavity or to enclose each fiber end in a sleeve 27 as indicated schematically in FIG. 5b.

In a physical embodiment we use a spectrometer fabricated by Ocean Optics of Dunedin, Fla. p/n USB2000 UV/Vis.

Not shown is the control means of a suitably programmed computer that controls illumination and scanning. Such means and the programming thereof are within the skill of the skilled instrument designer and require no further explication here.

In use, with the instrument open as shown in FIG. 1a, the eight lower anvils 30 are loaded each with a sample of fluid preferably using a pipette permitting simultaneous loading of all 8 samples. Then the instrument 10 is closed as shown in FIG. 1b, first to a close sample compression position (as taught in the prior Robertson patents). This spreads the samples and wets both the lower set of anvils 30 and the upper set of anvils 22. Then, as described in the prior Robertson patents, the two arms 16 and 24 are spaced apart a controlled distance in a substantially parallel relationship to draw each sample into a measuring column between the opposing ends of fibers 14 and 26. This establishes a substantially parallel relationship between the fiber ends forming the opposing anvils establishing an optical path between the wetted areas on each of the fiber ends The flash-lamp 12 is actuated as the light source, a measurement signal is formed in each measuring column, and fiber 34 is scanned across the eight ends 48 of fibers 26. Fiber 34 transmits each signal in turn to spectrometer 36 which in practice is connected to means such as a computer for information processing and output display as well as instrument sequencing.

Because upper arm 16 is much heavier than those in prior instruments described in the prior Robertson patents and application, improved means for actuating the relative motion between pivotally-mounted upper arm 16 and fixed arm 24 have been developed. One such implementation uses a DC servo motor 60 to activate a screw 61 that when turned controls the level of the upper arm when closed. The end of screw 61 bears on a suitable bushing 64 in surface 20 of upper arm 16.

Figure 3:
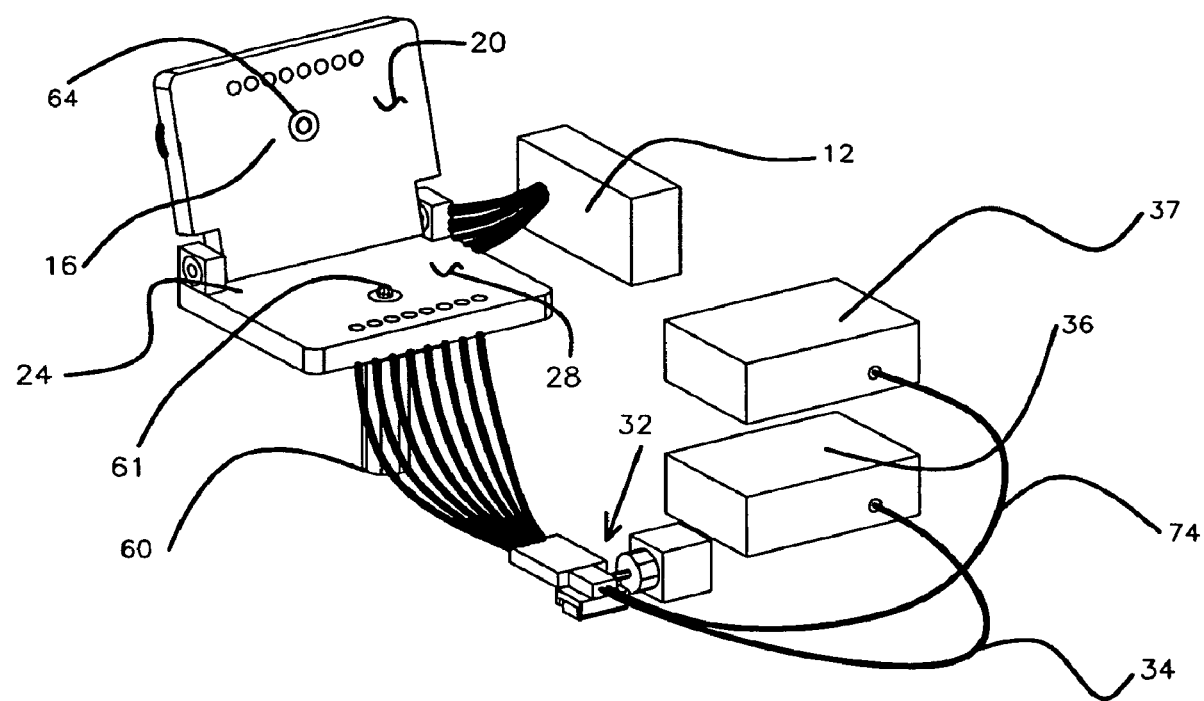
FIG. 3 shows the perspective view of the apparatus where more than one fiber is scanned across the sample measurement fiber each feeding a separate spectral analysis system.

In applications needing more complex spectral analysis, a second collecting fiber can be used to collect data simultaneously with the primary fiber as is shown in FIG. 3. Here the second fiber 74 is spaced one or more intervals away from the primary scanning fiber 34 and may be associated with a second spectrometer 37, or other optical measuring instrument as will be seen, as shown in the figure. If the spacing is one interval, then only a single spectrometer will be employed for measurement on either end of the scan. Such measurements could be used to extend the measurement wavelength range beyond that covered by a single spectrometer or the second instrument could be used for entirely different sorts of measurements like fluorescence, the latter requiring additional light sources if the measurement is to be made in the orthogonal illumination fashion of the fluorescence instrument of application PCT/US2006?00406. Multiple fiber measurements can also be used to decrease the time needed to make measurements on the multiple samples. More than 2 spectrometers can be similarly employed by using additional scanning fibers spaced at the same interval as the fiber end group 48.

Figure 4A:
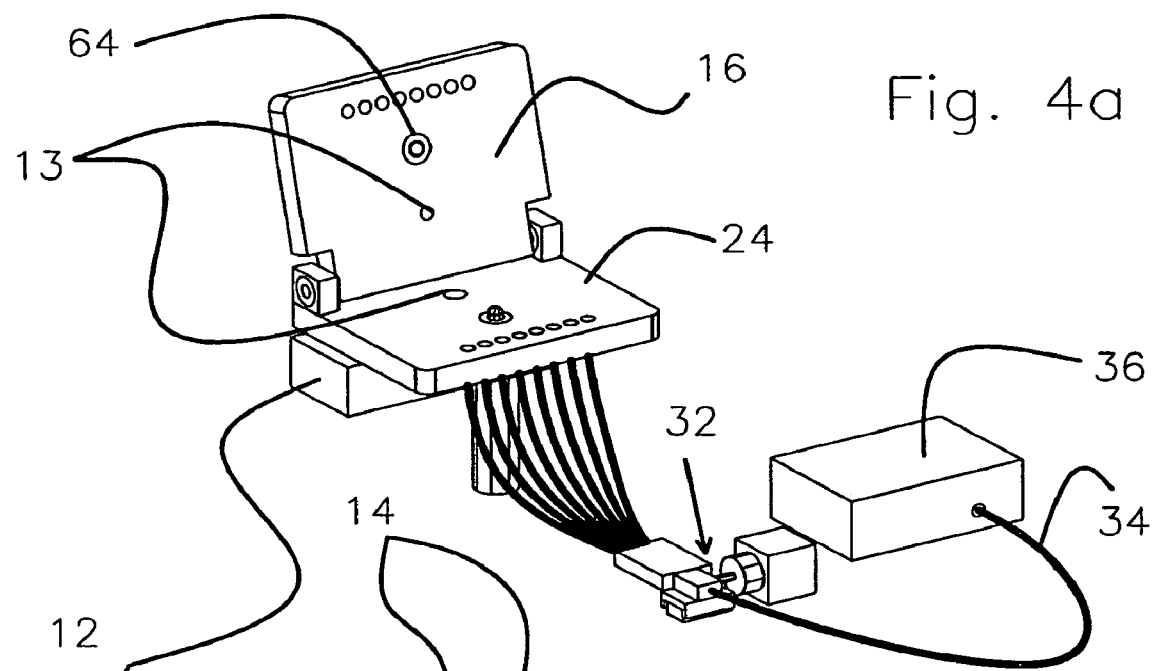
FIGS. 4a and b show an alternate arrangement for holding the source fibers to the moving arm of the apparatus with 4a showing the apparatus open without the source fibers and 4b showing the apparatus closed with the source fibers.
Figure 4B:
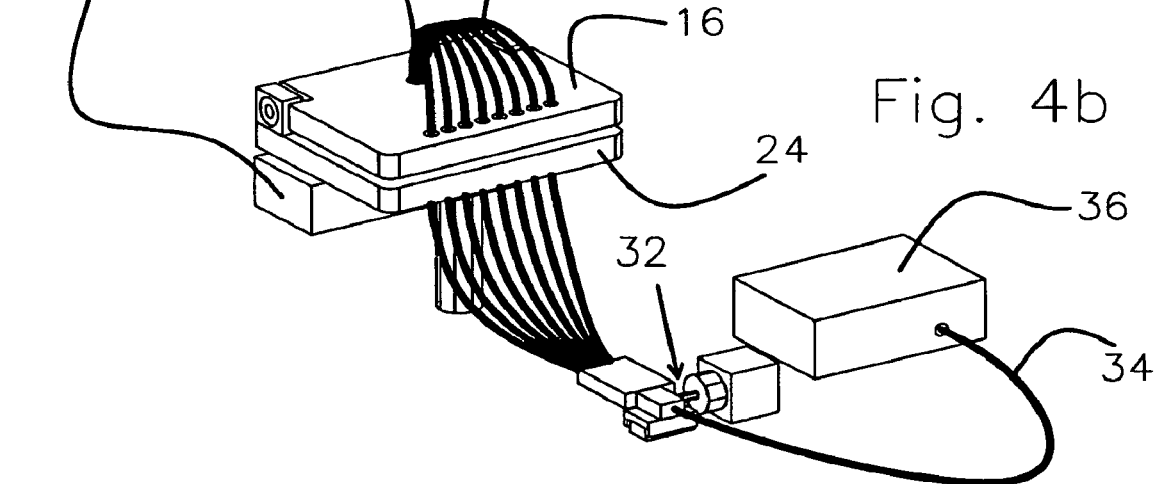

Additionally the supply fibers 14 connecting the moving upper arm 16 to the lamp 12 can be mounted entirely on the arm as is shown in FIG. 4a with the lamp 12 mounted directly to the lower arm 24. The fibers are coupled by passing through ports 13 in both the lower 24 and upper arm 16.

We claim:

1. An instrument for making optical measurements on a plurality of microliter samples contained by surface tension comprising:
    means for containing a plurality of microliter samples by surface tension between opposing, proximal-ends of a plurality of supply optical fibers and an equal plurality of proximal ends of receiving/ detecting optical fibers, said ends in a substantially parallel, spaced-apart relationship and establishing a columnar optical path between wetted areas on each of the opposing fiber ends for measuring signals;
    means for supplying light to the distal ends of the supply fibers;
    means for holding the distal ends of the receiving/detecting fibers in a spaced array;
    means for scanning the proximal ends of more than one scanning fiber across the spaced distal ends of the receiving/ detecting fibers; and
    more than one means connected to the distal ends of the more than one scanning fiber for accepting signals transmitted through the more than one scanning fiber and making optical measurements thereon, wherein optical measurements are made at more than one receiving/ detecting fiber end simultaneously using the more than one scanning fiber and more than one means for accepting signals and making optical measurements thereon.

2. The instrument of claim 1 wherein the measurements are spectrometric and the means for making measurements is a spectrometer.

3. The instrument of claim 1 wherein the measurements are fluorometric and the means for making measurements is a flourometer.

4. The instrument of claim 1 wherein the spaced array of the distal ends of the receiving/ detecting fibers is linear and the means for scanning is linear.

5. The instrument of claim 1 wherein the spaced array of the distal ends of the receiving/detecting fibers is toroidal and the means for scanning is rotary.

6. The instrument of claim 1 wherein there are first and second spectrometers and said second spectrometer measures an entirely different wavelength range than the first spectrometer.

7. The instrument of claim 1 wherein there are first and second means for making measurement and said second means for making measurements is other than a spectrometer.

8. The instrument of claim 7 wherein the second measuring means measures fluorescence.

9. The instrument of claim 1 wherein a plurality of measurements can be made simultaneously each on different samples.

10. The instrument of claim 1 wherein the means for containing the samples comprises a fixed, lower arm with the proximal ends of a plurality of receiving/detecting fibers finished slightly proud of the upper surface thereof to serve as anvils and a pivotally connected upper arm with the proximal ends of an equal plurality of supply fibers finished proud of the lower surface thereof to serve as opposing anvils said upper arm moveable to a substantially closed position to spread the samples and wet opposing anvil surfaces of fiber ends and then to a selected more open position to pull the samples into columns to establish optical paths for optical measurements, the proximal ends of said supply fibers attached to the moveable arm and said optical fibers fed through ports in both the upper and fixed arm with the distal ends of the supply fibers attached to the means for supplying light, said means attached to said lower fixed arm.

11. An instrument for making optical measurements on a plurality of samples, comprising:
a plurality of supply optical fibers;
a plurality of receiving/detecting optical fibers, each of the receiving/detecting optical fibers having a proximal end opposed to and spaced from a proximal end of a corresponding supply optical fiber, the distance between corresponding proximal ends of opposed receiving/detecting and supply optical fibers being controllable to draw each of the samples into a measuring column extending between the opposed proximal ends;
a light source for supplying light to the distal ends of the supply fibers;
a multiplexer, configured to receive and hold the distal ends of the plurality of receiving/detecting optical fibers in a spaced array, the multiplexer sequentially optically coupling different distal ends of the receiving/detecting optical fibers with a proximal end of a first scanning optical fiber and a second scanning optical fiber; and
an optical measuring instrument coupled to the distal end of the first scanning optical fiber for accepting signals transmitted through the first scanning optical fiber and making optical measurements thereon and a second optical measuring instrument coupled to the distal end of the second scanning optical fiber for accepting signals transmitted through the second scanning optical fiber and making optical measurements thereon, wherein the multiplexer serially optically couples the proximal end of the second scanning optical fiber to each of the distal ends of the receiving/detecting optical fibers, the proximal ends of the first scanning optical fiber and the second optical fiber being coupled, at any point in time, to the distal ends of different receiving/detecting optical fibers.

12. The instrument of claim 11, wherein the multiplexer includes a stepper motor linear actuator for sequentially bringing the proximal ends of the first scanning optical fiber and the second scanning optical fiber in optical alignment with a corresponding respective distal end of one of the receiving/detecting optical fibers.

13. The instrument of claim 11, wherein the distal ends of the receiving/detecting optical fibers are interleaved with the ends of a plurality of dead fibers.

14. The instrument of claim 11, wherein the proximal ends of the plurality of supply fibers and the plurality of receiving/detecting fibers are respectively secured to an upper arm and a fixed arm, the upper arm being movable with respect to the fixed arm so as to vary the distance between corresponding proximal ends of opposed receiving/detecting and supply optical fibers.

* * * * *